(12) United States Patent
Sung

(10) Patent No.: US 11,984,532 B2
(45) Date of Patent: May 14, 2024

(54) SEMICONDUCTOR DEVICE HAVING RECESSES FORMING AREAS

(71) Applicant: SUZHOU LEKIN SEMICONDUCTOR CO., LTD., Taicang (CN)

(72) Inventor: Youn Joon Sung, Seoul (KR)

(73) Assignee: SUZHOU LEKIN SEMICONDUCTOR CO., LTD., Taicang (CN)

( * ) Notice: Subject to any disclaimer, the term of this patent is extended or adjusted under 35 U.S.C. 154(b) by 590 days.

(21) Appl. No.: 17/256,585

(22) PCT Filed: Jun. 28, 2019

(86) PCT No.: PCT/KR2019/007884
§ 371 (c)(1),
(2) Date: Dec. 28, 2020

(87) PCT Pub. No.: WO2020/005009
PCT Pub. Date: Jan. 2, 2020

(65) Prior Publication Data
US 2021/0273134 A1    Sep. 2, 2021

(30) Foreign Application Priority Data

Jun. 29, 2018    (KR) .......................... 10-2018-0076017

(51) Int. Cl.
*H01L 33/22*    (2010.01)
*A61L 9/20*    (2006.01)
(Continued)

(52) U.S. Cl.
CPC ................ *H01L 33/22* (2013.01); *A61L 9/20* (2013.01); *H01L 33/382* (2013.01); *H01L 33/44* (2013.01);
(Continued)

(58) Field of Classification Search
CPC .. H01L 33/22; H01L 33/36–486; H01L 33/62
See application file for complete search history.

(56) References Cited

U.S. PATENT DOCUMENTS 11,527,677 B2 *   12/2022   Sung ..................... H01L 33/387
2018/0151778 A1    5/2018   Park et al.
(Continued)

FOREIGN PATENT DOCUMENTS

JP        2014-195055 A    10/2014
KR    10-2013-0112330 A    10/2013
(Continued)

OTHER PUBLICATIONS

WO 2017213455 A1, Chen et al., Machine Translation (Year: 2017).*

*Primary Examiner* — Andres Munoz
(74) *Attorney, Agent, or Firm* — Birch, Stewart, Kolasch & Birch, LLP

(57) ABSTRACT

A semiconductor device including a conductive substrate; a semiconductor structure including a first conductive type semiconductor layer, a second conductive type semiconductor layer, and an active layer arranged between the first conductive type semiconductor layer and the second conductive type semiconductor layer, and including a plurality of recesses; a first electrode electrically connecting the first conductive type semiconductor layer to the conductive substrate; a second electrode electrically connected to the second conductive type semiconductor layer; and an insulating layer arranged inside the plurality of recesses. The plurality of recesses include a first recess and a plurality of second recesses, the first electrode includes a plurality of protrusion electrodes extending to the inside of the second, the active layer includes an inactive area arranged between
(Continued)

the semiconductor structure and the first recess, and an active area arranged on the inner side of the first recess.

18 Claims, 10 Drawing Sheets

(51) Int. Cl.
  *H01L 33/38* (2010.01)
  *H01L 33/44* (2010.01)
  *H01L 33/48* (2010.01)
  *C02F 1/32* (2023.01)
(52) U.S. Cl.
  CPC ............ *H01L 33/486* (2013.01); *C02F 1/325* (2013.01); *C02F 2201/3222* (2013.01); *C02F 2303/04* (2013.01)

(56) References Cited

U.S. PATENT DOCUMENTS

| | | |
|---|---|---|
| 2018/0219133 A1 | 8/2018 | Park et al. |
| 2018/0323341 A1 | 11/2018 | Koo et al. |
| 2019/0181300 A1 | 6/2019 | Park et al. |

FOREIGN PATENT DOCUMENTS

| | | | |
|---|---|---|---|
| KR | 10-2015-0142740 A | 12/2015 | |
| KR | 10-2016-0138789 A | 12/2016 | |
| KR | 10-2017-0024534 A | 3/2017 | |
| KR | 10-2017-0052105 A | 5/2017 | |
| KR | 10-2018-0006821 A | 1/2018 | |
| KR | 10-2018-0028338 A | 3/2018 | |
| WO | WO-2017213455 A1 * | 12/2017 | ............. H01L 33/00 |

* cited by examiner

SEMICONDUCTOR DEVICE HAVING RECESSES FORMING AREAS

CROSS REFERENCE TO RELATED APPLICATIONS

This application is the National Phase of PCT International Application No. PCT/KR2019/007884, filed on Jun. 28, 2019, which claims priority under 35 U.S.C. 119(a) to Patent Application No. 10-2018-0076017, filed in the Republic of Korea on Jun. 29, 2018, all of which are hereby expressly incorporated by reference into the present application.

TECHNICAL FIELD

An embodiment relates to a semiconductor device.

BACKGROUND ART

A semiconductor device including a compound such as GaN, AlGaN, or the like has many advantages such as having wide and easily adjustable band gap energy, and thus can be variously used as a light emitting device, a light receiving device, various diodes, and the like.

Specifically, a light emitting device such as a light emitting diode or laser diode using group III-V or II-VI compound semiconductor materials can implement various colors such as red, green, blue, ultraviolet rays, and the like through the development of thin film growth technology and device materials, can implement white light with good efficiency by using fluorescent materials or combining colors, and has advantages of low power consumption, semi-permanent lifespan, quick response time, safety, environmental friendliness, and the like in comparison with conventional light sources such as a fluorescent lamp, an incandescent lamp, and the like.

In addition, when a light receiving device such as a photodetector or solar cell is also manufactured using group III-V or II-VI compound semiconductor materials, due to the development of device materials, light in various wavelength ranges from a gamma ray range to a radio wavelength range can be used by absorbing light in various wavelength ranges and generating a photocurrent. In addition, the light receiving device has advantages of quick response time, safety, environmental friendliness, and easy adjustment of the device materials, and thus can be easily used for power control, ultra-high frequency circuits, or communication modules.

Accordingly, application of the semiconductor device is being expanded to a transmission module of an optical communication means, a light emitting diode backlight replacing a cold cathode fluorescence lamp (CCFL) that constitutes a backlight of a liquid crystal display (LCD) device, a white light emitting diode lighting device capable of replacing a fluorescent or an incandescent bulb, car headlights, traffic lights, a sensor which senses gas or fire, and the like. Further, the application of the semiconductor device can be expanded to a high frequency application circuit, other power control devices, and a communication module.

Specifically, a light emitting device which emits light in an ultraviolet wavelength range can be used for curing, medical, and sterilizing purposes by performing a curing or sterilizing action.

Although research on an ultraviolet light emitting device is active recently, the ultraviolet light emitting device has a problem of being difficult to be implemented in a vertical type, and a problem in that optical output is lowered due to oxidization by peeling and moisture.

Further, in order to generate light in the ultraviolet wavelength band, since an aluminum composition increases, there is a problem in that current dispersion efficiency is lowered. Accordingly, there is a problem in that light emitting efficiency is lowered at a side surface of a semiconductor structure.

DISCLOSURE

Technical Problem

An embodiment is directed to providing a semiconductor device having excellent current dispersion efficiency.

Further, an embodiment is directed to providing a semiconductor device resistant to peeling and moisture.

In addition, an embodiment is directed to providing a semiconductor device with improved emission uniformity.

In addition, an embodiment is directed to providing a semiconductor device having excellent optical output.

Problems to be solved by the present invention are not limited to the above-described problems, and purposes and effects understood from solutions and embodiments which will be described below are also included.

Technical Solution

A semiconductor device according to one aspect of the present invention includes: a conductive substrate; a semiconductor structure arranged on the conductive substrate, including a first conductive type semiconductor layer, a second conductive type semiconductor layer, and an active layer arranged between the first conductive type semiconductor layer and the second conductive type semiconductor layer, and including a plurality of recesses which pass through the second conductive type semiconductor layer and the active layer, and up to a partial region of the first conductive type semiconductor layer; a first electrode configured to electrically connect the first conductive type semiconductor layer and the conductive substrate; a second electrode electrically connected to the second conductive type semiconductor layer; and an insulating layer arranged in the plurality of recesses, wherein the plurality of recesses include a first recess extending along an outer surface of the semiconductor structure and a plurality of second recesses arranged at an inner side of the first recess, the first electrode includes a plurality of protruding electrodes extending to the inside of the second recess so as to be electrically connected to the first conductive type semiconductor layer, the active layer includes an inactive area arranged between a side surface of the semiconductor structure and the first recess, and an active area arranged on the inner side of the first recess, and the emission intensity of the inactive area is less than the emission intensity of the active area.

Advantageous Effects

According to an embodiment, the optical output of a semiconductor device can be improved.

Further, a semiconductor device with improved reliability can be manufactured by blocking a light emitting region of the semiconductor device from external moisture or other contaminants.

Various useful advantages and effects of the present invention are not limited to the above and can be relatively

MODES OF THE INVENTION

Figure 1:
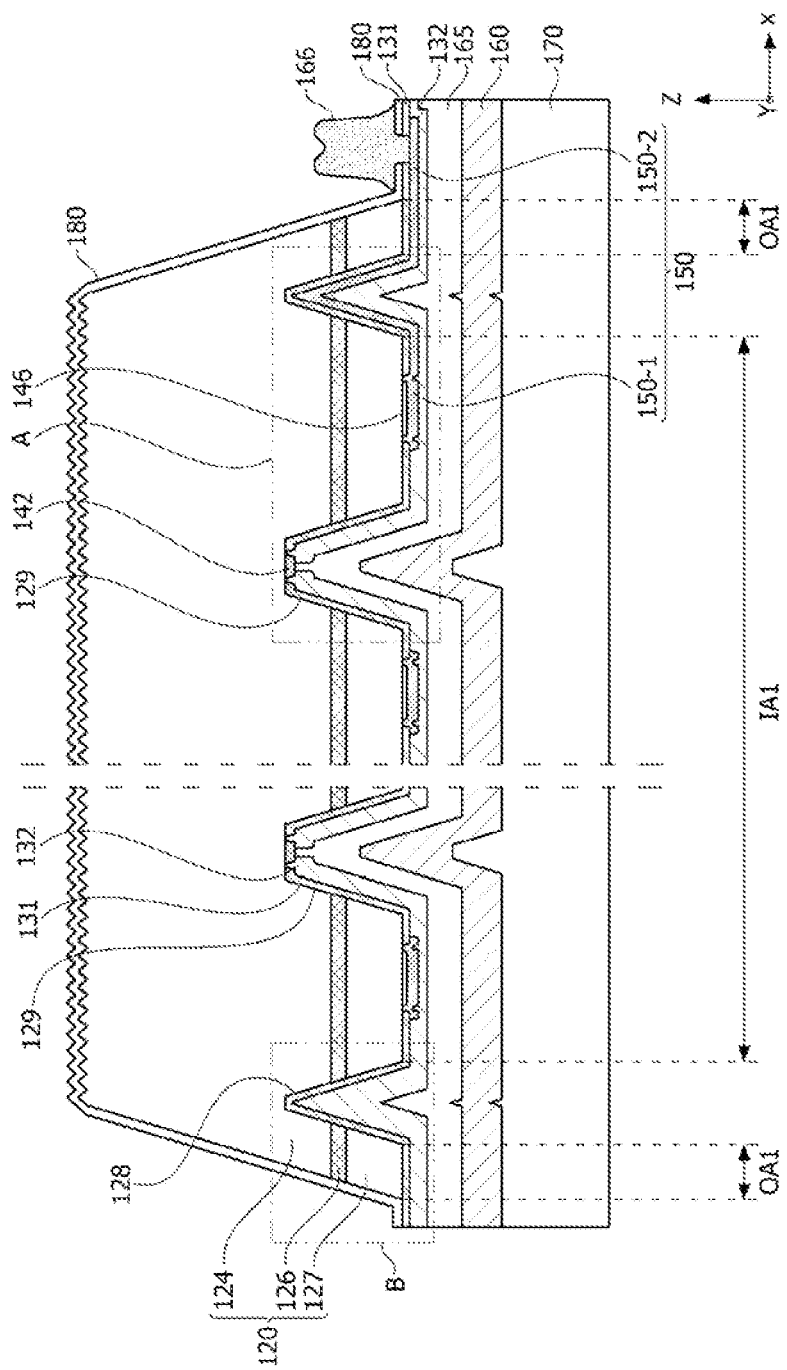
FIG. 1 is a conceptual diagram of a semiconductor device according to a first embodiment of the present invention.

Since the present invention may be variously changed and have various embodiments, particular embodiments will be exemplified and described in the drawings. However, it should be understood that the present invention is not limited to the particular embodiments and includes all changes, equivalents, and substitutes within the spirit and the scope of the present invention.

Further, it should be understood that, although the terms "second," "first," and the like may be used herein to describe various elements, the elements are not limited by the terms. The terms are only used to distinguish one element from another. For example, a first element may be termed a second element, and similarly, a second element may be termed a first element without departing from the scope of the present invention. The term "and/or" includes any one or any combination among a plurality of associated listed items.

When predetermined components are mentioned as being "linked," or "connected" to other components, the components may be directly linked or connected to other components, but it should be understood that additional components may be present therebetween. On the other hand, when the predetermined components are mentioned as being "directly linked," or "directly connected" to other components, it should be understood that no additional components are present between the above-described components.

Terms used in the present application are used solely to describe the particular embodiments and not to limit the present invention. The singular form is intended to also include the plural form, unless the context clearly indicates otherwise. It should be further understood that the terms "include," "including," "provide," "providing," "have," and/or "having" specify the presence of stated features, integers, steps, operations, elements, components, and/or groups thereof but do not preclude the presence or addition of one or more other features, integers, steps, operations, elements, components, and/or groups thereof.

Unless otherwise defined, all terms including technical or scientific terms used in the present application have meanings which are the same as those of terms generally understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments will be described in detail with reference to the accompanying drawing drawings, the same reference numerals are applied to the same or corresponding elements, and redundant description thereof will be omitted.

A semiconductor structure according to an embodiment of the present invention may emit light in an ultraviolet wavelength band. For example, the semiconductor structure may emit light in a near ultraviolet wavelength band (ultraviolet (UV)-A), may emit light in a far ultraviolet wavelength band (UV-B), and may emit light in a deep ultraviolet wavelength band (UV-C). The wavelength band may be determined by a composition ratio of Al in a semiconductor structure. Further, the semiconductor structure may output light of various wavelengths with different light intensities, and a peak wavelength of light having the strongest intensity relative to the intensity of other wavelengths among the wavelengths of emitted light may be a near ultraviolet ray, a far ultraviolet ray, or a deep ultraviolet ray.

For example, the light in the near ultraviolet wavelength band (UV-A) may have a wavelength ranging from 320 nm to 420 nm, the light in the far ultraviolet wavelength band (UV-B) may have a wavelength ranging from 280 nm to 320 nm, and the light in the deep ultraviolet wavelength band (UV-C) may have a wavelength ranging from 100 nm to 280 nm.

Figure 2:
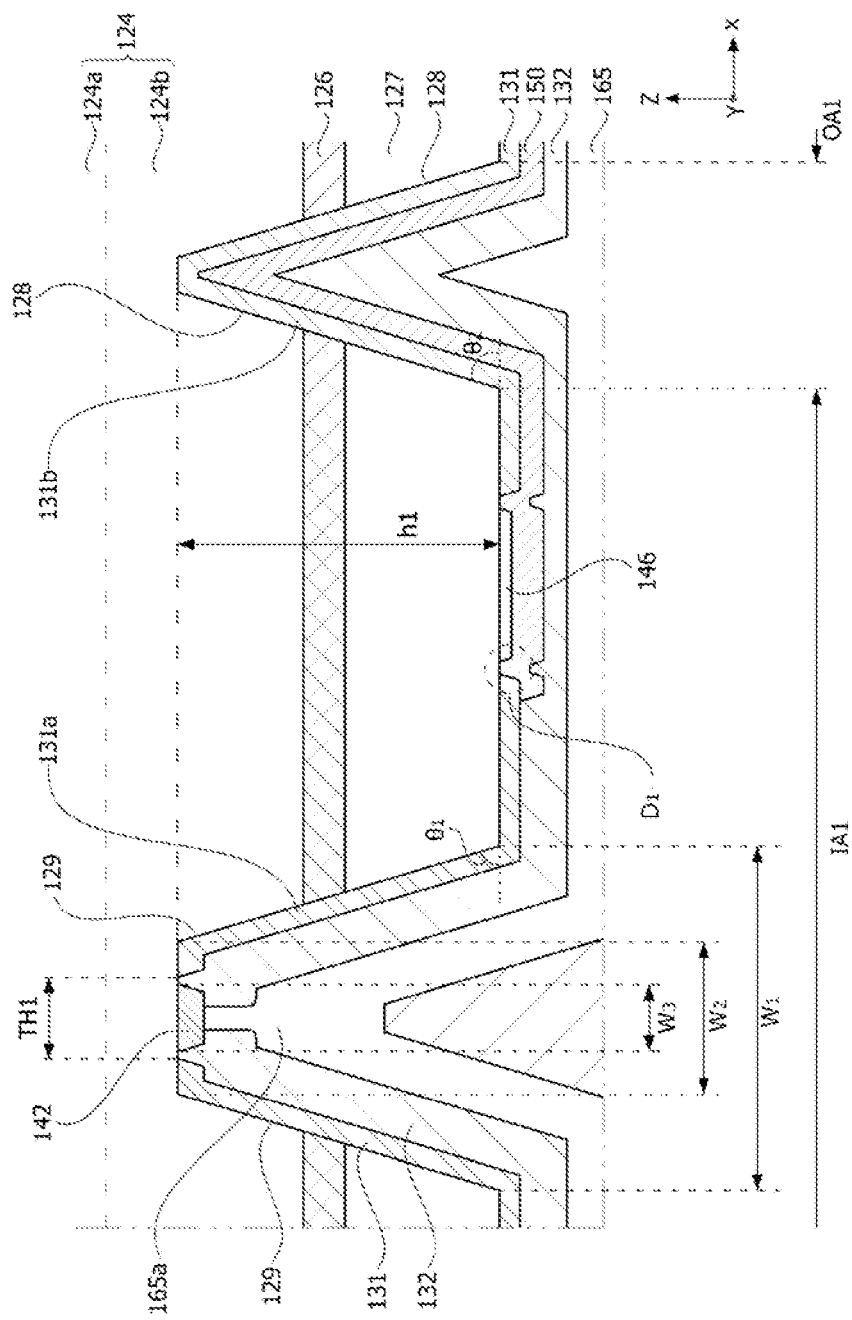
FIG. 2 is an enlarged view of portion A in FIG. 1.
Figure 3:
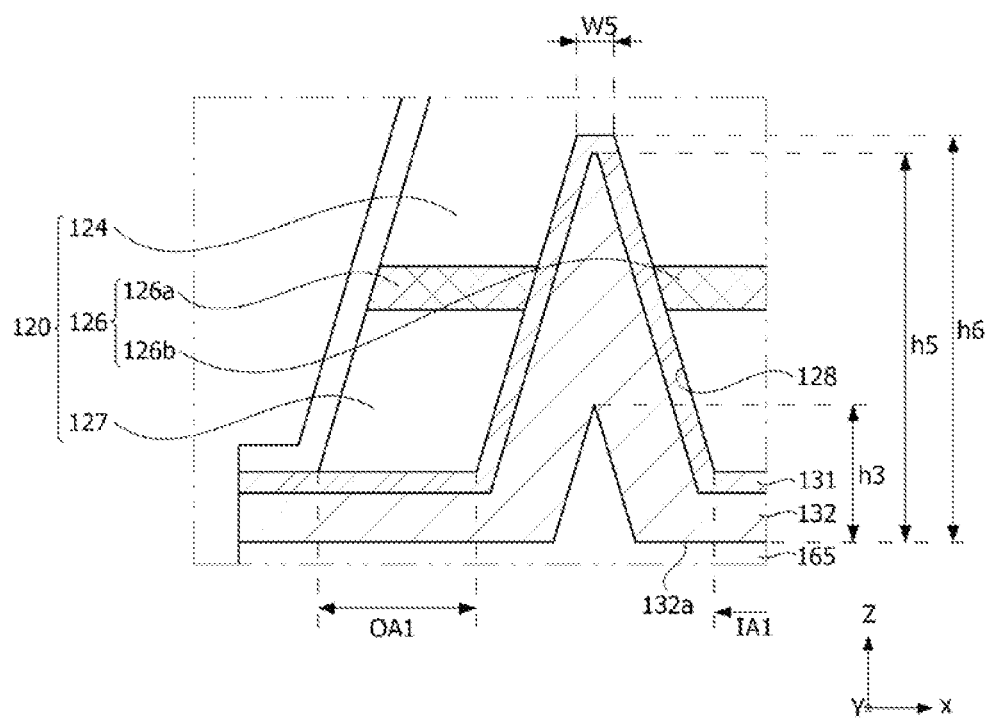
FIG. 3 is an enlarged view of portion B in FIG. 1.

FIG. 1 is a conceptual diagram of a semiconductor device according to a first embodiment of the present invention, FIG. 2 is an enlarged view of portion A in FIG. 1, and FIG. 3 is an enlarged view of portion B in FIG. 1.

Referring to FIGS. 1 and 2, a semiconductor device 10 according to the embodiment may include a conductive substrate 170, a semiconductor structure 120 including a first conductive type semiconductor layer 124, a second conductive type semiconductor layer 127, and an active layer 126, a first connection electrode 142 electrically connected to the first conductive type semiconductor layer 124, and a second connection electrode 146 electrically connected to the second conductive type semiconductor layer 127.

The first conductive type semiconductor layer 124 may be implemented with a group III-V or II-VI compound semiconductor, and may be doped with a first dopant. The first conductive type semiconductor layer 124 may be selected from semiconductor materials having a composition formula of $In_{x1}Al_{y1}Ga_{1-x1-y1}N$ (x1 is 0 to 1, y1 is 0 to 1, and x1+y1 is 0 to 1), for example, AlGaN, InGaN, InAlGaN, and the like. Further, the first dopant may be an n-type dopant such as Si, Ge, Sn, Se, and Te. When the first dopant is an n-type dopant, the first conductive type semiconductor layer 124 doped with the first dopant may be an n-type semiconductor layer.

The active layer 126 may be arranged between the first conductive type semiconductor layer 124 and the second conductive type semiconductor layer 127. The active layer 126 may be a layer in which electrons (or holes) injected through the first conductive type semiconductor layer 124 and holes (or electrons) injected through the second conductive type semiconductor layer 127 are recombined.

As the electrons and the holes recombine in the active layer 126, the electrons transition to a low energy level, and light having a wavelength corresponding to the band gap energy of a well layer to be described below and included in the active layer 126 may be generated. A wavelength of light having a relatively largest intensity among wavelengths of light emitted by the semiconductor device may be ultraviolet rays, and the ultraviolet rays may be near ultraviolet rays, far ultraviolet rays, and deep ultraviolet rays which are described above.

The active layer 126 may have one structure among a single well structure, a multiple well structure, a single quantum well structure, a multi quantum well (MQW) structure, a quantum dot structure, and a quantum wire structure, and the structure of the active layer 126 is not limited thereto.

The second conductive type semiconductor layer 127 may be formed on the active layer 126, may be implemented with a group III-V or II-VI compound semiconductor, and may be doped with a second dopant. The second conductive type semiconductor layer 127 may be formed of a semiconductor material having a composition formula of $In_{x5}Al_{y2}Ga_{1-x5-y2}N$ (x5 is 0 to 1, y2 is 0 to 1, and x5+y2 is 0 to 1), or a material selected from AlGaN, AlInN, AlGaAs, GaP, GaAs, GaAsP, AlGaInP. When the second dopant is a p-type dopant such as Mg, Zn, Ca, Sr, Ba, or the like, the second conductive type semiconductor layer 127 doped with the second dopant may be a p-type semiconductor layer.

An electron blocking layer (not shown) may be arranged between the active layer 126 and the second conductive type semiconductor layer 127. The electron blocking layer (not shown) blocks the escape to the second conductive type semiconductor layer 127 without recombination of electrons supplied from the first conductive type semiconductor layer 124 to the active layer 126 to emit light in the active layer 126 and thus it is possible to increase the probability that electrons and holes recombine in the active layer 126. An energy band gap of the electron blocking layer (not shown) may be larger than an energy band gap of the active layer 126 and/or the second conductive type semiconductor layer 127.

The first conductive type semiconductor layer 124, the active layer 126, and the second conductive type semiconductor layer 127 may all include aluminum (Al). Accordingly, compositions of the first conductive type semiconductor layer 124, the active layer 126, and the second conductive type semiconductor layer 127 may all be AlGaN. However, the present invention is not necessarily limited thereto, and a composition of a semiconductor layer may be appropriately adjusted according to an output wavelength.

The semiconductor structure 120 may include a first recess 128 and a plurality of second recesses 129 which pass through the second conductive type semiconductor layer 127 and the active layer 126 and are arranged up to a partial region of the first conductive type semiconductor layer 124.

The first recess 128 may continuously extend along a side surface of the semiconductor structure 120. The first recess 128 may be a single recess extending along an outer surface of the semiconductor structure 120 to form a closed loop, but is not limited thereto, and may be divided into a plurality of recesses.

The semiconductor structure 120 may be classified into a first region OA1 arranged at an outer side of the first recess 128 and a second region IA1 arranged at an inner side of the first recess 128 by the first recess 128.

The plurality of second recesses 129 may be arranged at the inner side of the first recess 128. The second recess 129 may have a first connection electrode 142 arranged therein to serve as a path for injecting a current into the first conductive type semiconductor layer 124.

The first region OA1 may be a region outside the first recess 128, and the second region IA1 may be an inner region of the first recess 128. Further, the first region OA1 is a non-emission region in which electron and hole combination does not occur, and the second region IA1 is a region where the current is dispersed and thus may be a light emitting region.

The active layer 126 has an inactive area in the first region OA1 and an active area in the second region OA2. In the active area, the electrons and the holes are injected through the first conductive type semiconductor layer 124 and the second conductive type semiconductor layer 127 to generate light having a maximum intensity in the ultraviolet wavelength band. In the inactive area of the active layer 126, the excited electrons due to absorption of light irradiated from the active area or the outside may weakly emit light through recombination. Accordingly, the active area may have a greater emission intensity than the inactive area.

A passivation layer 180 surrounding side surfaces and an upper surface of the semiconductor structure 120 may be peeled from the semiconductor structure 120 due to heat generated by the operation of the semiconductor device, external high temperature, high humidity, a difference in thermal expansion coefficient with the semiconductor structure 120, and the like. Alternatively, cracks or the like may occur in the passivation layer 180.

When peeling, cracks, or the like occur in the passivation layer 180, the semiconductor structure 120 may be oxidized by external moisture, contaminants, or the like which penetrate into the semiconductor structure 120 from the outside.

In the case of an ultraviolet light emitting device, since an Al composition in the active layer 126 is relatively high, it may be more susceptible to oxidization. Accordingly, when a sidewall of the semiconductor structure 120 is exposed due to cracks or the like, the active layer 126 is rapidly oxidized and thus optical output may be reduced.

However, according to the embodiment, the first recess 128 may be arranged between the active layer 126 of the first region OA1 and the active layer 126 of the second region IA1. Further, a distance between the active layer 126 of the first region OA1 and the active layer 126 of the second region IA1 may be increased by the first recess 128. Accordingly, even when the active layer 126 of the first region OA1 is oxidized, the active layer 126 of the second region IA1 may be prevented from being oxidized by the first recess 128.

A ratio of an area of the first recess 128 and an area of the second recess 129 may be 1:6 to 1:10. When the area ratio is less than 1:6 (for example, 1:5), since a ratio of the second recess 129 in the semiconductor device decreases, optical output may be deteriorated. Further, when the area ratio is greater than 1:10, since a maximum width of the first recess 128 decreases, it may be difficult to effectively block humidity introduced from the outside or crack propagation.

Referring to FIG. 2, a first insulating layer 131 may be arranged under the semiconductor structure 120 to electrically insulate the first connection electrode 142 from the active layer 126 and the second conductive type semiconductor layer 127.

The first insulating layer 131 may be formed by selecting at least one from the group consisting of $SiO_2$, $SixOy$, $Si_3N_4$, $SixNy$, $SiOxNy$, $Al_2O_3$, $TiO_2$, AlN, and the like, but is not limited thereto. The first insulating layer 131 may be formed as a single layer or multiple layers. For example, the first insulating layer 131 may be a distributed Bragg reflector (DBR) having a multilayer structure including Si oxide or a Ti compound. However, the present invention is not necessarily limited thereto, and the first insulating layer 131 may include various reflective structures.

The first insulating layer 131 may include a first insulating part 131b arranged in the first recess 128 and a second insulating part 131a arranged in the second recess 129. The first insulating part 131b and the second insulating part 131a may be connected to each other on a lower surface of the second conductive type semiconductor layer 127.

The first insulating part 131b may be entirely arranged in the first recess 128 to electrically insulate a first conductive layer 165 from the first conductive type semiconductor layer 124. Accordingly, the current may hardly be dispersed in the active layer 126 arranged at an outer side of the first recess 128. Since the first insulating part 131b is arranged in the first recess 128, oxidization of a side surface of the active layer 126 may be more effectively prevented.

The second insulating part 131a may be arranged in the second recess 129 and a through hole TH1 may be formed. The first connection electrode 142 may be arranged in the through hole TH1 of the second insulating part 131a to be electrically connected to the first conductive type semiconductor layer 124. Specifically, the first connection electrode 142 may be arranged on a relatively low aluminum layer 142b in the first conductive type semiconductor layer 124, but is not limited thereto.

A height h1 of the second recess 129 may be the same as a height h1 of the first recess 128. Further, an inclination angle θ1 of the second recess 129 may be the same as an inclination angle θ2 of the first recess 128. However, the present invention is not necessarily limited thereto, and the first recess 128 and the second recess 129 may have different heights, and the first recess 128 and the second recess 129 may have different inclination angles. Further, a width of the second recess 129 in a first direction (an X-axis direction) may be greater than a width of the first recess 128 in the first direction.

For example, the second recess 129 should be formed up to a region of the first conductive type semiconductor layer 124 having low contact resistance with the first connection electrode 142, whereas it may be sufficient if the first recess 128 has a height capable of separating the active layer 126. Accordingly, the height of the second recess 129 may be greater than that of the first recess 128. Conversely, in order to effectively prevent side surface oxidization, the height of the first recess 128 may be greater than the height of the second recess 129.

The first connection electrode 142 may be arranged in the second recess 129 to be electrically connected to the first conductive type semiconductor layer 124. Further, the second connection electrode 146 may be arranged on a bottom surface of the second conductive type semiconductor layer 127 to be electrically connected to the second conductive type semiconductor layer 127.

The first connection electrode 142 and the second connection electrode 146 may be ohmic electrodes. The first connection electrode 142 and the second connection electrode 146 may be formed by including at least one of indium tin oxide (ITO), indium zinc oxide (IZO), indium zinc tin oxide (IZTO), indium aluminum zinc oxide (IAZO), indium gallium zinc oxide (IGZO), indium gallium tin oxide (IGTO), aluminum zinc oxide (AZO), antimony tin oxide (ATO), gallium zinc oxide (GZO), IZO nitride (IZON), Al—Ga ZnO (AGZO), In—Ga ZnO (IGZO), ZnO, IrOx, RuOx, NiO, RuOx/ITO, Ni/IrOx/Au or Ni/IrOx/Au/ITO, Ag, Ni, Cr, Ti, Al, Rh, Pd, Ir, Sn, In, Ru, Mg, Zn, Pt, Au, and Hf, but are not limited to these materials. For example, the first connection electrode 142 may have a plurality of metal layers (for example, Cr/Al/Ni), and the second connection electrode 146 may be ITO.

The first conductive layer 165 may include a plurality of protruding electrodes 165a penetrating through the second recess 129 and a second insulating layer 132 to be electrically connected to the plurality of first connection electrodes 142. Accordingly, the first conductive layer 165 and the plurality of first connection electrodes 142 may be defined as a first electrode.

The first conductive layer 165 may be made of a material having excellent reflectance. For example, the first conductive layer 165 may include a metal such as Ti, Ni, Al, or the like. For example, when the first conductive layer 165 includes aluminum, the ultraviolet light emitted from the active layer 126 may be reflected upward.

A second conductive layer 150 may cover the second connection electrode 146. Accordingly, a second connection electrode pad 166, the second conductive layer 150, and the second connection electrode 146 may form one electrical channel. Accordingly, the second connection electrode 146 and the second conductive layer 150 may be defined as a second electrode. The second conductive layer 150 may be arranged in a separation space D1 between the second connection electrode 146 and the first insulating layer 131 to be Schottky bonded to the first conductive type semiconductor layer 124. Accordingly, current dispersion efficiency may be improved.

The second conductive layer 150 may be formed of a material having good adhesion with the first insulating layer 131, may be formed of at least one material selected from the group consisting of materials such as Cr, Ti, Ni, Au, and the like, or an alloy thereof, and may be formed as a single layer or a plurality of layers.

The second conductive layer 150 may be arranged under the first insulating layer 131. The second conductive layer 150 may be arranged between the first insulating layer 131 and the second insulating layer 132. Accordingly, the second conductive layer 150 may be protected from penetration of external moisture or contaminants by the first insulating layer 131 and the second insulating layer 132. Further, the second conductive layer 150 may be arranged in the semiconductor device, and may be surrounded by the first insulating layer 131 and the second insulating layer 132 so as not to be exposed at the outermost side of the semiconductor device.

The second conductive layer 150 may be arranged on the conductive substrate 170 and may be arranged between the electrode pad, and the semiconductor structure 120 and the substrate 170. Further, the second conductive layer 150 may be arranged between the first insulating layer 131 and the second connection electrode 146.

The second conductive layer 150 may include a first conductive region 150-1 and a second conductive region 150-2. First, the first conductive region 150-1 may be arranged in the first recess 128, and the second conductive region 150-2 may extend from the second-first conductive region 150-1 toward the electrode pad.

The second conductive layer 150 is arranged so that most of the second conductive layer 150 is surrounded by the first recess 128, but may be arranged to extend from a portion adjacent to the electrode pad 166 to the electrode pad 166 arranged outside the semiconductor structure 120. That is, the first conductive region 150-1 may be surrounded by the first recess 128, and the second conductive region 150-2 may extend from the first conductive region 150-1 to the electrode pad 166 arranged outside the semiconductor structure 120.

The second insulating layer 132 may electrically insulate the first conductive layer 165 and the second conductive layer 150. The first insulating layer 131 and the second insulating layer 132 may be made of the same material or different materials.

The second insulating layer 132 may be arranged in each of the first recess 128 and the second recess 129. Accordingly, both the first insulating layer 131 and the second insulating layer 132 may be arranged in the first recess 128 and the second recess 129. Accordingly, even when a defect occurs in one of the first insulating layer 131 and the second insulating layer 132, the remaining insulating layer may prevent the penetration of external moisture and/or other contaminants.

For example, when the first insulating layer 131 and the second insulating layer 132 are configured as one layer, defects such as cracks may easily propagate in the thickness direction. Accordingly, external moisture or contaminants may penetrate into the semiconductor structure 120 through defects exposed to the outside.

However, according to the embodiment, since a separate second insulating layer 132 is arranged on the first insulating layer 131, it may be difficult for defects formed in the first insulating layer 131 to propagate to the second insulating layer 132. That is, an interface between the first insulating layer 131 and the second insulating layer 132 may serve to shield the propagation of defects.

A bonding layer 160 may be arranged along a lower surface of the semiconductor structure 120 and a shape of the second recess 129. The bonding layer 160 may include a conductive material. For example, the bonding layer 160 may include a material selected from the group consisting of gold, tin, indium, aluminum, silicon, silver, nickel, and copper, or an alloy thereof.

The conductive substrate 170 may include a metal or a semiconductor material. The conductive substrate 170 may be a metal having excellent electrical conductivity and/or thermal conductivity. In this case, heat generated during the operation of the semiconductor device may be quickly dissipated to the outside. Further, the first connection electrode 142 may receive a current from the outside through the conductive substrate 170.

The conductive substrate 170 may include a material selected from the group consisting of silicon, molybdenum, silicon, tungsten, copper, and aluminum, or an alloy thereof.

The passivation layer 180 may be arranged on the upper surface and the side surfaces of the semiconductor structure 120. A thickness of the passivation layer 180 may range from 200 nm to 500 nm. When the thickness is 200 nm or more, electrical and optical reliability of the device may be improved by protecting the device from external moisture or foreign matter, and when the thickness is less than 500 nm, stress applied to the semiconductor device may be reduced, and it is possible to improve a problem in which costs of the semiconductor device increase due to deterioration of the optical and electrical reliability of the semiconductor device or an increase in process time of the semiconductor device.

An unevenness may be formed on the upper surface of the semiconductor structure 120. This unevenness may enhance extraction efficiency of light emitted from the semiconductor structure 120. The unevenness may have different average heights depending on the UV wavelength, and in the case of UV-C, light extraction efficiency may be enhanced when the height is approximately 300 nm to 800 nm and the average height is approximately 500 nm to 600 nm.

Referring to FIG. 3, a maximum height h3 of the bonding layer 165 from the lowermost surface 132a of the first recess 128 may be 0.4 µm to 0.6 µm. Further, a maximum height h5 of the second insulating layer 132 from the lowermost surface 132a of the first recess 128 in a vertical direction (a Z direction) may be 1.7 µm to 2.1 µm. In addition, a maximum height h6 of the first insulating layer 131 from the lowermost surface 132a of the first recess 128 in the vertical direction may be 2.4 µm to 2.6 µm. In addition, an upper surface of the first recess 128 may have a horizontal minimum width W5 of 2 µm to 8 µm.

An area of a first active layer 126a arranged at the outer side of the first recess 128 may be wider than an area of a second active layer 126b arranged at the inner side of the first recess 128.

A ratio of the maximum area of the semiconductor structure 120 and the maximum area of the first recess 128 may be 1:0.01 to 1:0.03. When the ratio of the maximum area of the semiconductor structure 120 and the maximum area of the first recess 128 is less than 1:0.01, it may be difficult to prevent oxidization of the active layer 126 by contaminants. Further, when the ratio is larger than 1:0.03, light efficiency may be deteriorated The first recess 128 may have a maximum separation distance (the same as OA1) from the outer surface of the semiconductor structure 120 in a range of 3 µm to 5 µm. When the maximum separation distance is less than 3 µm, the penetration of external moisture may be facilitated, and when the maximum separation distance is larger than 5 µm, there is a problem in that a non-light emitting region is widened. However, the maximum separation distance may be modified depending on the size of the semiconductor device or semiconductor structure 120.

Figure 4:
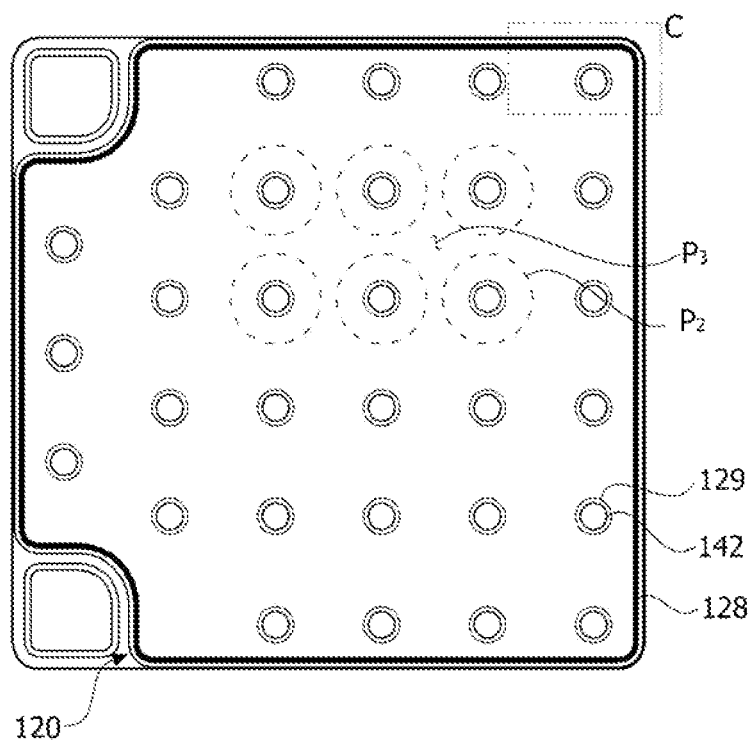
FIG. 4 is a plan view of the semiconductor device according to the first embodiment of the present invention.
Figure 5:
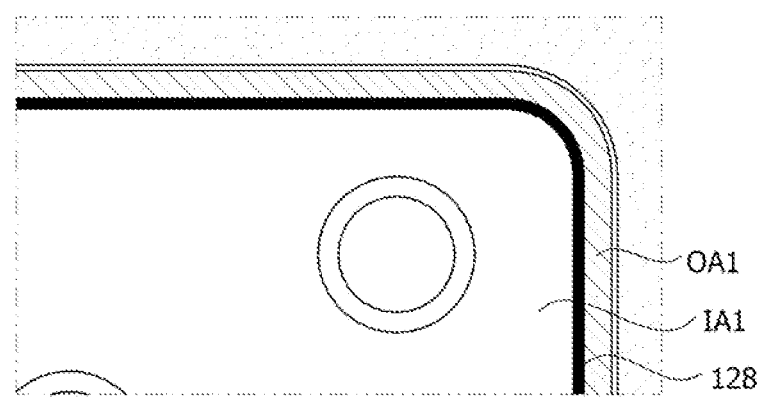
FIG. 5 is an enlarged view of portion C in FIG. 4.
Figure 6:
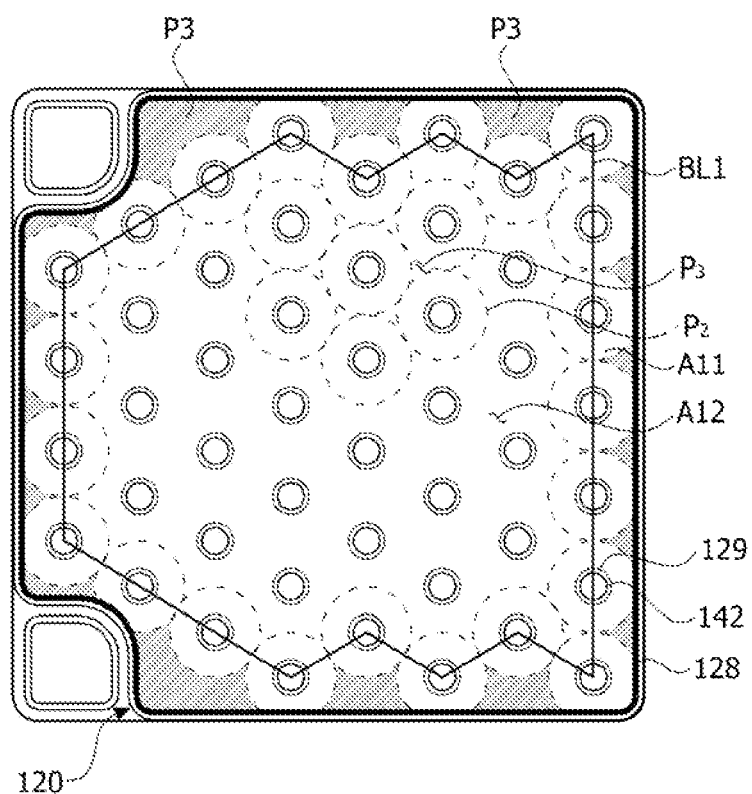
FIG. 6 is a plan view of a semiconductor device according to a second embodiment of the present invention.
Figure 7:
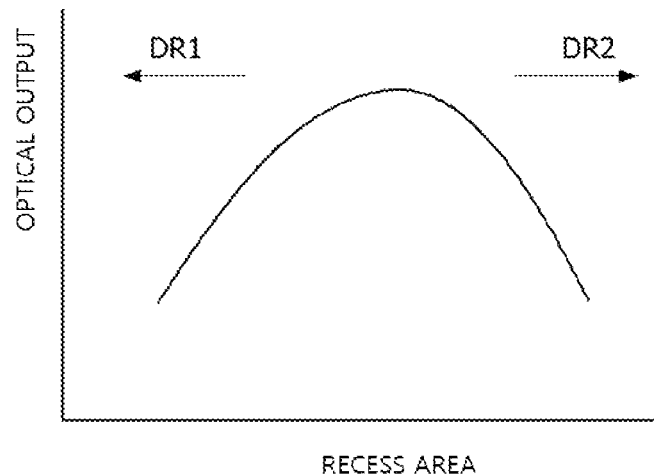
FIG. 7 is a graph illustrating a relationship between the number of recesses and optical output.

FIG. 4 is a plan view of the semiconductor device according to the first embodiment of the present invention, FIG. 5 is an enlarged view of portion C in FIG. 4, FIG. 6 is a plan view of a semiconductor device according to a second embodiment of the present invention, and FIG. 7 is a graph illustrating a relationship between the number of recesses and optical output.

Referring to FIGS. 4 and 5, the first recess 128 may be arranged along the outer surface of the semiconductor structure 120 to form a closed-loop in a plan view. Accordingly, the semiconductor structure 120 may be partitioned into the first region OA1 and the second region IA1 by the closed-loop made of the first recess 128. However, the present invention is not necessarily limited thereto, and a plurality of first recesses 128 may be spaced apart from each other along an edge of the semiconductor structure 120.

The first region OA1 may be a region outside the first recess 128, and the second region IA1 may be an inner region of the first recess 128. The first region OA1 may be an inactive area where electron and hole combination does not occur, and the second region IA1 may be an active area arranged at the inner side of the first recess 128 to emit light. Accordingly, emission intensity of the first region OA1 may be lower than that of the second region IA1.

In the active area IA1, the electrons and the holes may be injected through the first conductive type semiconductor layer 124 and the second conductive type semiconductor layer 127 to generate light having the maximum intensity in the ultraviolet wavelength band.

In the inactive area OA1 of the active layer 126, the excited electrons due to absorption of light irradiated from the active area or the outside may emit light through the recombination. However, the emission intensity of the inactive area may be very weak compared to emission intensity of the active area. Alternatively, the inactive area may not emit light at all.

The semiconductor structure 120 may be oxidized by external moisture, contaminant, or the like which penetrates the semiconductor structure 120 from the outside. Since the Al composition in the active layer 126 of the ultraviolet light emitting device is relatively high, the ultraviolet light emitting device may be more susceptible to oxidization. The first recess 128 may block the active layer 126 of the second region IA1 from oxidization when the active layer (126a in FIG. 3) of the first region OA1 is oxidized.

Since the semiconductor structure 120 has high band gap energy while generating ultraviolet light, current dispersion characteristics of the semiconductor structure 120 may be deteriorated, and an effective light emitting region P2 may be reduced. Accordingly, substantial current dispersion may be achieved in the second region IA1. Accordingly, even when the semiconductor device has the first recess 128, it is possible to maintain sufficient optical output.

In addition, the first recess 128 may limit a region where oxidization occurs due to moisture or the like in the active layer 126 to the first region OA1 and protect the second region IA1 where the effective light emitting region P2 is located to maintain optical output.

The effective light emitting region P2 may be defined as a region up to a boundary point where the current density is 40% or less based on the current density in the first connection electrode 142 having the highest current density. Further, the effective light emitting region P2 may be defined as a region which is 2 to 5 times a diameter of the first connection electrode 142. For example, a distance of 5 μm to 40 μm from a center of an inner recess 129a may be defined as the boundary point. However, the effective light emitting region P2 may vary depending on a level of an injection current and the composition of Al.

A low current density region P3 outside the effective light emitting regions P2 has a low current density and thus may hardly contribute to light emission. Accordingly, in the ultraviolet semiconductor device, it is possible to enhance optical output by further arranging the first connection electrode 142 in the low current density region P3 having a low current density.

In the case of FIG. 6, it can be seen that an area of the low current density region P3 has been further reduced due to an increase in the number of first connection electrodes 142 in a center portion. Generally, in the case of a GaN semiconductor layer, since the current dispersion characteristics are relatively excellent, it is preferable to minimize the areas of the second recess and the first connection electrode. This is because the area of the active layer decreases as the areas of the second recess and the first connection electrode increase.

However, in the case of the embodiment, in order to emit ultraviolet light, the active layer should include Al, and in order to secure crystallinity, the first conductive type semiconductor layer and the second conductive type semiconductor layer need to contain Al having a high composition.

Accordingly, there is a problem in that the Al composition of the first and second conductive type semiconductor layers increases, and thus resistance increases, and the current diffusion characteristics are deteriorated. Accordingly, it may be preferable to increase the number of first connections electrodes even when the area of the active layer is sacrificed.

As shown in FIG. 7, when the number of second recesses 129 and the number of first connection electrodes 142 are too large (in a DR2 direction), since the area of the active layer 126 may be reduced, the emission intensity may be rather lowered. Accordingly, it is necessary to appropriately adjust the number of second recesses 129.

Referring to FIG. 6, even when the number of recesses increases, since it is difficult to sufficiently arrange the first connection electrodes 142 at the edge of the semiconductor structure 120, a region having relatively low light emission intensity may be generated. That is, even when the number of recesses increases, since the current is not injected into the edge of the semiconductor structure 120, the low current density region P3 may be partially generated.

Accordingly, in the second region IA1, the low current density region arranged outside the second recesses 129 arranged at the outermost side may be formed, and the emission intensity in the low current density region may be greater than that of the first region OA1, and may be lower than that of a center region of the semiconductor structure 120 where the second recess 129 is arranged.

The second region IA1 may be classified into a second-first region A11 arranged at an outer side based on a closed-loop BL1 which connects centers of the plurality of second recesses 129 arranged at the outermost side, and a second-second region A12 arranged at an inner side of the closed-loop BL1. The second region may be an active area.

The plurality of second recesses 129 may be classified into inner recesses and outer recesses. The inner recesses may be defined as recesses in which the number of closest second recesses 129 is less than N, and the outer recesses may be defined as recesses in which the number of closest second recesses 129 is less than N.

For example, the inner recess may be defined as a recess surrounded by six recesses, and the outer recess may be defined as a recess surrounded by two to five recesses.

An emission intensity ratio of the second-second region A12 and the second-first region A11 may be 1:0.5 to 1:0.8. When the emission intensity ratio is 1:0.5 or more, since the areas of the first recess 128 and the first connection electrode 142 increase, the emission intensity of the second-first region A11 increases, and when the emission intensity ratio is 1:0.8 or less, since the area of the active layer 126 capable of emitting light may be secured, it is possible to prevent an excessive reduction of the optical output.

Accordingly, the emission intensity of the second-first region A11 may be lower than that of the second-second region A12 and may be higher than that of an outer region (the first region) of the first recess 128.

Figure 8:
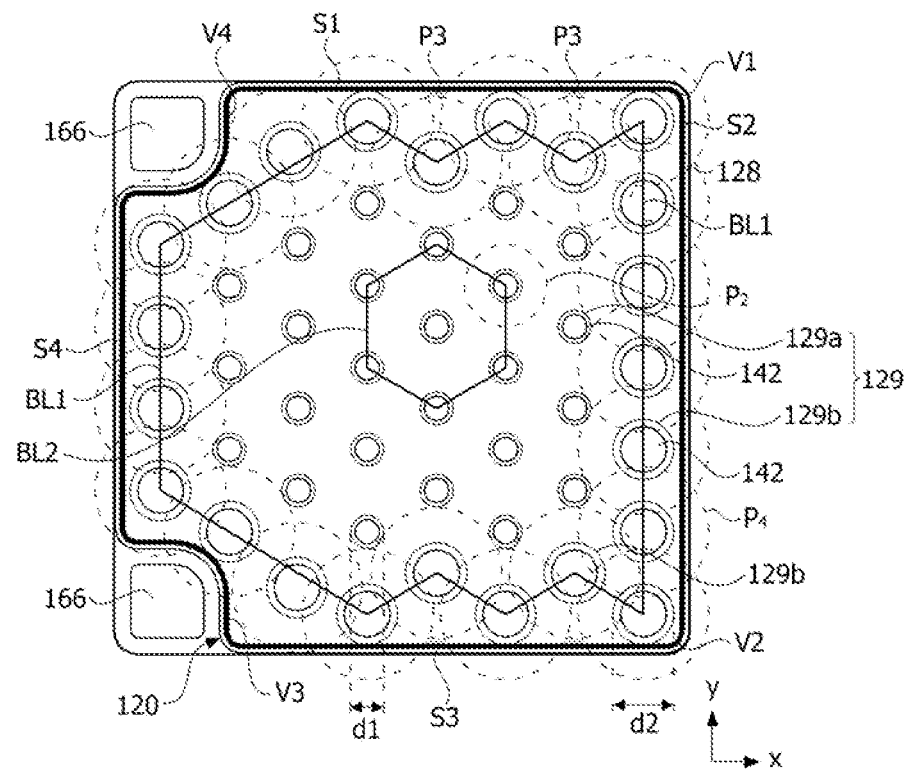
FIG. 8 is a plan view of a semiconductor device according to a third embodiment of the present invention.
Figure 9:
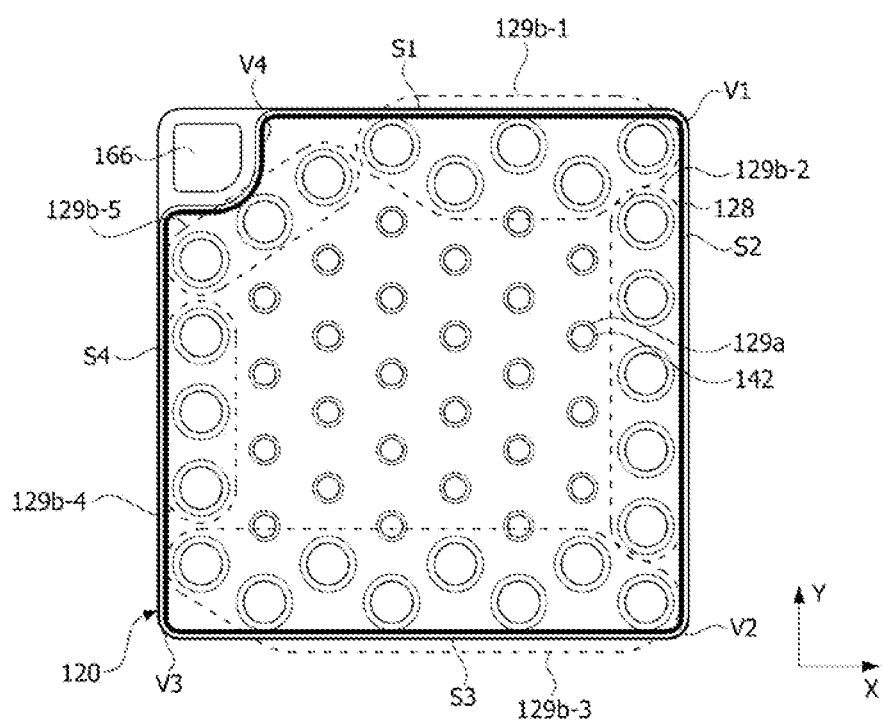
FIG. 9 is a plan view of a semiconductor device according to a fourth embodiment of the present invention.
Figure 10:
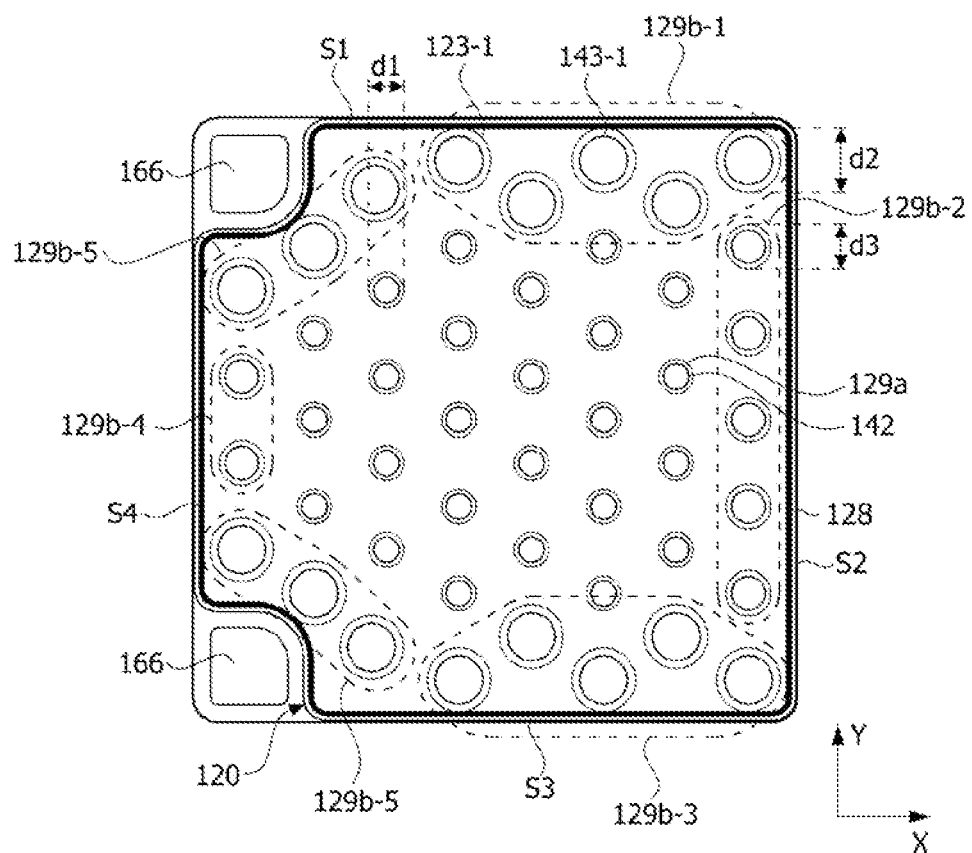
FIG. 10 is a plan view of a semiconductor device according to a fifth embodiment of the present invention.

FIG. 8 is a plan view of a semiconductor device according to a third embodiment of the present invention, FIG. 9 is a plan view of a semiconductor device according to a fourth embodiment of the present invention, and FIG. 10 is a plan view of a semiconductor device according to a fifth embodiment of the present invention.

Referring to FIG. 8, the plurality of second recesses 129 may include a plurality of inner recesses 129a in which the number of closest second recesses 129 is N and a plurality of outer recesses 129b in which the number of closest second recesses 129 is less than N. The outer recesses 129b may be the second recesses 129 closest to side surfaces S1, S2, S3, and S4 of the semiconductor structure 120.

For example, the inner recess 129a may be surrounded by six closest recesses 129. That is, distances between the six recesses 129 forming vertices of a hexagon BL2 and the second recess 129 arranged in the hexagon may be the same. However, the present invention is not necessarily limited thereto, and the inner recess 129a may be a structure (for example, a pentagonal structure or an octagonal structure) surrounded by closest 5 or 8 second recesses 129.

In the outer recess 129b, the number of closest recesses may be less than N. For example, when the number of closest recesses surrounding the inner recess 129a is 6, the outer recess 129b may be surrounded by two to five recesses. The outer recesses 129b may be surrounded by two second recesses 129 or may be surrounded by four second recesses 129.

The outer recesses 129b may be defined as recesses arranged at the closest positions along the side surfaces S1, S2, S3, and S4 of the semiconductor structure 120. That is, the outer recesses 129b may be a set of the second recesses 129 arranged at the outermost side of the plurality of second recesses 129. Accordingly, since the recesses may not be arranged between the outer recesses 129b and the side surfaces S1, S2, S3, S4 of the semiconductor structure 120, the number of recesses surrounding the outer recess 129b may be less than the number of recesses surrounding the inner recess 129a.

The outer recess 129b may have at least one of a diameter and a shape different from that of the inner recess 129a. The outer recess 129b may have a different diameter or a different shape from the inner recess 129a. Further, both the shape and diameter may be different.

A diameter d2 of the outer recess 129b may be larger than a diameter d1 of the inner recess 129a. As described above, since the number of second recesses 129 around the outer recesses 129b is relatively small, the current is not dispersed to the side surfaces of the semiconductor structure 120 and thus the low current density region P3 may be generated. Accordingly, as diameters of the outermost outer recess 129b and the first connection electrode 142 are increased, the current may be dispersed to the side surfaces of the semiconductor structure 120. Accordingly, emission intensity at the side surface of the semiconductor structure 120 may increase. Further, since the low current density region P3 at the side surface of the semiconductor structure 120 is reduced, light uniformity may also increase.

Accordingly, an emission intensity ratio of an outer region of the closed-loop BL1 extending the centers of the plurality of outer recesses 129b and an inner region of the closed-loop BL1 may be controlled to be a range from 1:0.5 to 1:0.8.

A diameter ratio (d1:d2) of the inner recess 129a and the outer recess 129b may be 1:1.2 to 1:2. When the diameter ratio is 1:1.2 or more, since an area of the first connection electrode 142 arranged inside the outer recess 129b is widened, the current is dispersed to the side surface of the semiconductor structure 120 to emit light. Further, when the diameter ratio is smaller than 1:2, an area of the outer recess 129b is too wide to prevent a light emitting area from decreasing.

The semiconductor structure 120 may include includes a first side surface S1 and a third side surface S3 facing each other in a plan view, a second side surface S2 and a fourth side surface S4 facing each other in a plan view, a first edge portion V1 which connects the first side surface S1 and the second side surface S2, a second edge portion V2 which connects the second side surface S2 and the third side surface S3, a third edge portion V3 which connects the third side surface S3 and the fourth side surface S4, and a fourth edge portion V4 which connects the fourth side surface S4 and the first side surface S1.

In this case, at least one of the third edge portion V3 and the fourth edge portion V4 may include a concave portion facing the electrode pad 166. In the embodiment, an example in which the concave portion is formed in each of the third edge portion V3 and the third edge portion V3 is described, but the concave portion may be formed only in one of the third edge portion V3 and the fourth edge portion V4.

For example, as shown in FIG. 9, the concave portion may be formed only in the fourth edge portion V4.

In order to increase the number of recesses and the number of first connection electrodes 142, it may be advantageous to have only one electrode pad. However, when only one electrode pad is arranged, since an area of the pad is relatively small, current dispersion efficiency may be deteriorated. Further, since resistance increases, current injection efficiency may decrease when a high current is applied.

Current injection efficiency may be defined as a ratio of an amount reaching the active layer 126 among the total amount of current applied to an optical device from the outside, but is not necessarily limited thereto. That is, the number of electrode pads may be appropriately adjusted according to characteristics and use of the corresponding semiconductor device.

Referring to FIG. 9, the outer recesses 129b may include a plurality of first outer recesses 129b-1 arranged along the first side surface S1, a plurality of second outer recesses 129b-2 arranged along the second side surface S2, a plurality of third outer recesses 129b-3 arranged along the third side surface S3, a plurality of fourth outer recesses 129b-4 arranged along the fourth side surface S4, and a plurality of fifth outer recesses 129b-5 arranged along the concave portion. The same recess is marked with a dotted line.

In this case, the plurality of first outer recesses 129b-1 have different shortest distances from the first side surface S1, the plurality of second outer recesses 129b-2 have the same shortest distance from the second side surface S2, the plurality of third outer recesses 129b-3 have different shortest distances from the third side surface S3, the plurality of fourth outer recesses 129b-4 have the same shortest distance from the fourth side surface S4, and the plurality of fifth outer recesses 129b-5 may have different shortest distances from the concave portion.

In the embodiment, the first outer recesses 129b-1 and the third outer recesses 129b-3 may be arranged in a zigzag manner in the first direction. Further, the second outer recesses 129b-2 and the fourth outer recesses 129b-4 may be arranged parallel to the side surface of the semiconductor structure 120 in a second direction.

Referring to FIG. 10, the diameter d2 of the first outer recess 129b-1 and the third outer recess 129b-3 may be greater than a diameter d3 of the second outer recess 129b-2 and the fourth outer recess 129b-4. The first outer recesses 129b-1 and the third outer recesses 129b-3 may be a set of recesses 123-1 having a first diameter, and the second outer recesses 129b-2 and the fourth outer recesses 129b-4 may be a set of recesses 123-2 having a second diameter. Accordingly, the area of the first connection electrode 142 arranged in the recess 123-1 having the first diameter may be greater than the area of the first connection electrode 142 arranged in the recess 123-2 having the second diameter.

Since an interval between the first outer recesses 129b-1 is wider than an interval between the second outer recesses 129b-2, the diameter d2 of the first outer recess 129b-1 may be formed larger than the diameter d3 of the second outer recess 129b-2 to compensate for this. Similarly, the diameter d2 of the third outer recess 129b-3 may be greater than the diameter d2 of the fourth outer recess 129b-4.

That is, the first outer recesses 129b-1 with a relatively wide interval have a wide diameter to disperse the current to the side surface of the semiconductor structure 120, and the second outer recesses 129b-2 with a relatively narrow interval may have a small diameter to prevent an unnecessary reduction of the light emitting area.

The diameter ratio (d1:d2) of the inner recess 129a and the first outer recess 129b-1 may be 1:1.4 to 1:2.0. When the diameter ratio (d1:d2) is greater than 1:1.4, since the area of the first outer recess 129b-1 increases, the current may be dispersed to the side surface of the semiconductor structure 120. Further, when the diameter ratio (d1:d2) is less than 1:2.0, the area of the first outer recess 129b-1 is too large to prevent an excessive reduction of the light emitting area.

A diameter ratio (d1:d3) of the inner recess 129a and the second outer recess 129b-2 may be 1:1.2 to 1:1.4. When the diameter ratio (d1:d3) is greater than 1:1.2, since the area of the second outer recess 129b-2 increases, current may be dispersed to the side surface of the semiconductor structure 120. Further, when the diameter ratio (d1:d3) is less than 1:1.4, the area of the second outer recess 129b-2 is too large to prevent an excessive reduction of the light emitting area.

Figure 11:
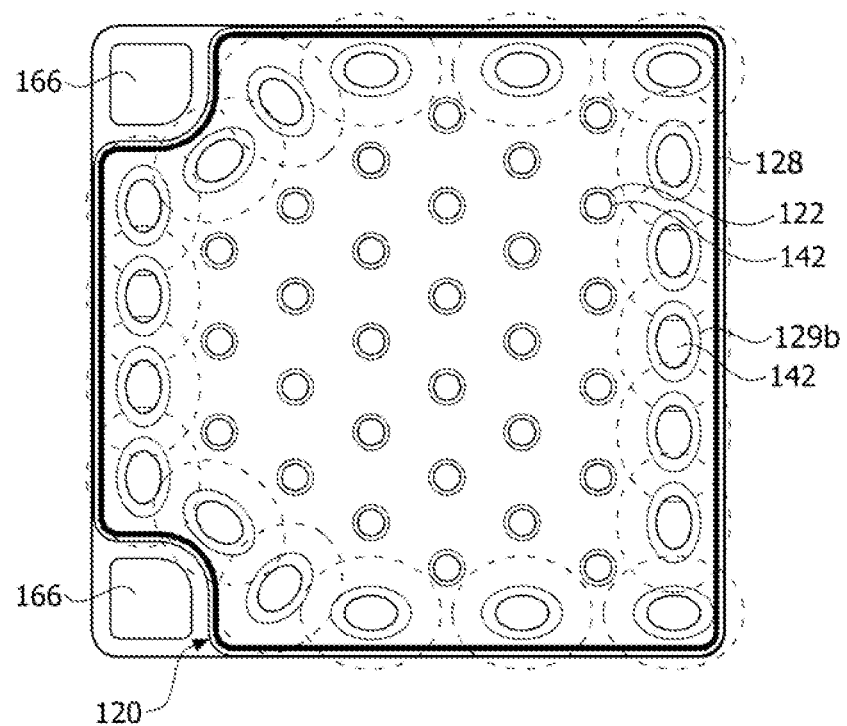
FIG. 11 is a plan view of a semiconductor device according to a sixth embodiment of the present invention.
Figure 12:
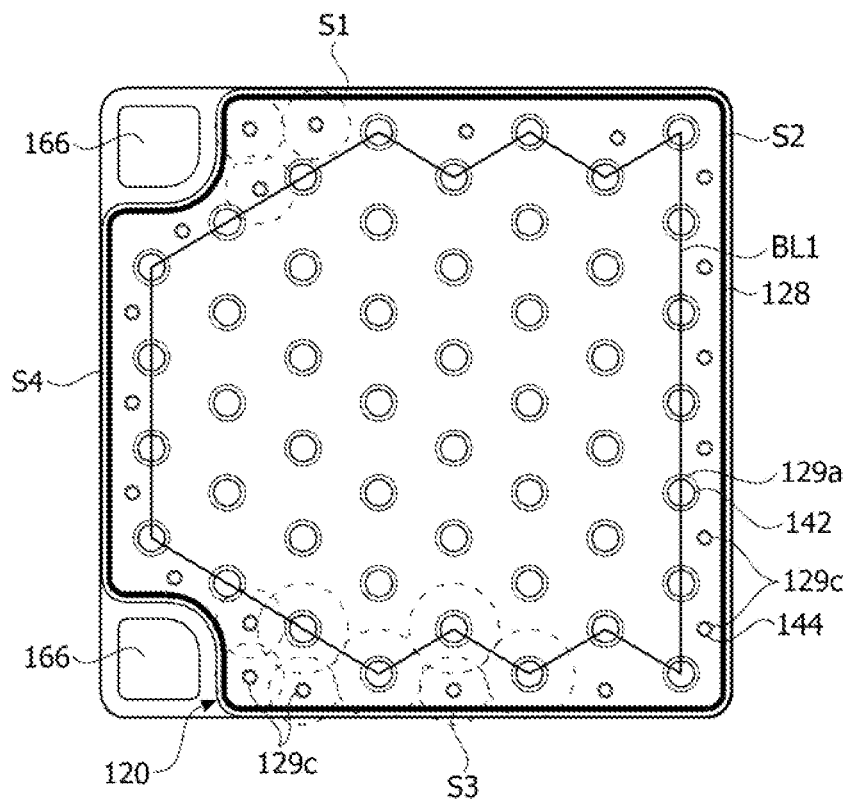
FIG. 12 is a plan view of a semiconductor device according to a seventh embodiment of the present invention.

FIG. 11 is a plan view of a semiconductor device according to a sixth embodiment of the present invention, and FIG. 12 is a plan view of a semiconductor device according to a seventh embodiment of the present invention.

Referring to FIG. 11, a shape of the outer recess 129b may be different from a shape of the inner recess 129a. For example, the outer recess 129b may have an oval shape. In this case, since the current injection efficiency may increase up to the adjacent region, the light emitting area may be widened. However, the present invention is not limited thereto, and the shape of the outer recess 129b may be appropriately modified to increase a current injection area.

Referring to FIG. 12, the plurality of second recesses 129 according to the embodiment may include a plurality of inner recesses 129a in which the number of closest second recesses 129 is N, a plurality outer recesses 129b in which the number of closest second recesses 129 is less than N, and a plurality of third recesses 129c arranged between the plurality of outer recesses 129b.

For example, the inner recess 129a may be surrounded by six closest recesses 129. The closest recesses may have the same diameter as the inner recess 129a. That is, distances between the six recesses 129 forming vertices of a hexagon and the second recess 129 arranged in the hexagon may be the same. However, the present invention is not necessarily limited thereto, and the inner recess 129a may be a structure (for example, a pentagonal structure or an octagonal structure) surrounded by closest 5 or 8 recesses.

In the outer recess 129b, the number of closest recesses may be less than N. The closest recesses, the inner recess 129a, and the outer recess 129b may have the same diameter. That is, the third recess 129c has a different diameter, and thus may be excluded from the closest recesses.

For example, when the number of closest recesses surrounding the inner recess 129a is 6, the outer recess 129b may be surrounded by two to five recesses. The outer recess 129b may be surrounded by two second recesses or may be surrounded by four second recesses.

The third recesses 129c may be arranged between the plurality of outer recesses 129b. The third recesses 129c may be arranged outside the closed-loop BL1 which connects the centers of the plurality of outer recesses 129b. Since the plurality of inner recesses 129a are densely arranged inside the closed-loop BL1, emission intensity may be relatively strong. Accordingly, the third recesses 129c may be arranged outside the closed-loop BL1, where emission intensity is relatively low.

Since the third recess 129c is formed smaller in size than the diameters of the inner recess 129a and the outer recess 129b, the diameter of the first connection electrode 142 arranged in the third recess 129c may also be smaller than the diameter of the first connection electrode 142 arranged in the first and second recesses 128 and 129.

According to the embodiment, since the third recess 129c is arranged at a point where emission intensity is weak and thus disperses the current, the emission intensity may be improved and overall light uniformity may be improved.

A shape of the third recess 129c may be variously modified. For example, the third recess 129c may have a shape different from those of the inner recess 129a and the outer recess 129b. For example, each of the inner recess 129a and the outer recess 129b may have a circular shape, while the third recess 129c may have an oval shape.

Figure 13:
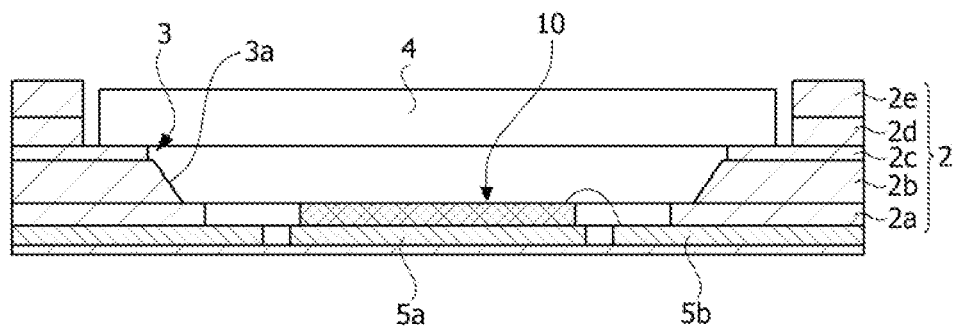
FIG. 13 is a conceptual diagram of a semiconductor device package according to one embodiment of the present invention.

FIG. 13 is a conceptual diagram of a semiconductor device package according to one embodiment of the present invention.

Referring to FIG. 13, the semiconductor device package may include a body 2 having a groove 3 formed therein, a semiconductor device 1 arranged in the body 2, and a pair of lead frames 5a and 5b arranged in the body 2 and electrically connected to the semiconductor device 1. The semiconductor device 1 may include all of the above-described configurations.

The body 2 may include a material or coating layer which reflects ultraviolet light. The body 2 may be formed by laminating a plurality of layers 2a, 2b, 2c, 2d, and 2e. The plurality of layers 2a, 2b, 2c, 2d, and 2e may be the same material or may include different materials.

The groove 3 may be formed to be wider as a distance from the semiconductor device increases, and a step 3a may be formed on an inclined surface.

A light transmission layer 4 may cover the groove 3. The light transmission layer 4 may be formed of a glass material, but is not limited thereto. The light transmission layer 4 is not particularly limited as long as it is a material capable of effectively transmitting ultraviolet light. The inside of the groove 3 may be an empty space.

The semiconductor device may be applied to various types of light source devices. For example, the light source device may be a concept including a sterilization device, a curing device, a lighting device, a display device, a vehicle lamp, and the like. That is, the semiconductor device may be applied to various electronic devices arranged in a case to provide light.

The sterilization device may sterilize a desired region by including the semiconductor device according to the embodiment. The sterilization device may be applied to household appliances such as a water purifier, an air conditioner, a refrigerator, and the like, but is not limited thereto. That is, the sterilization device may be applied to all various products (for example, a medical device) which require sterilization.

For example, the water purifier may be provided with the sterilization device according to the embodiment to sterilize circulating water. The sterilization device is arranged in a nozzle or an outlet through which the water circulates to irradiate ultraviolet rays. In this case, the sterilization device may include a waterproof structure.

The curing device may cure various types of liquid by including the semiconductor device according to the embodiment. The liquid may be a concept including all various materials which are cured when irradiated with ultraviolet rays. For example, the curing device may cure various types of resins. Alternatively, the curing device may be applied to cure cosmetic products such as a manicure.

The lighting device may include a light source module including a substrate and the semiconductor device of the embodiment, a heat dissipation part which dissipates heat from the light source module, and a power supply part which processes or converts an electrical signal provided from the outside to provide the electrical signal to the light source module. Further, the lighting device may include a lamp, a head lamp, a street light, or the like.

The display device may include a bottom cover, a reflective plate, a light emitting module, a light guide plate, an optical sheet, a display panel, an image signal output circuit, and a color filter. The bottom cover, the reflection plate, the light emitting module, the light guide plate, and the optical sheet may constitute a backlight unit.

The reflective plate may be arranged on the bottom cover, and the light emitting module may emit light. The light guide plate is arranged in front of the reflection plate to guide the light emitted from the light emitting module to the front, and the optical sheet may include a prism sheet and the like, and may be arranged in front of the light guide plate. The display panel may be arranged in front of the optical sheet, the image signal output circuit may supply an image signal to the display panel, and the color filter may be arranged in front of the display panel.

Although the above-described embodiments are mainly described with reference to the embodiments of the present invention, the above are only exemplary, and it should be understood that those skilled in the art may variously perform modifications and applications within the principle of the embodiments. For example, elements specifically shown in the embodiments may be modified. Further, differences related to modifications and changes should be understood as being included in the scope of the present invention defined in the appended claims.

The invention claimed is:

1. A semiconductor device comprising:
a conductive substrate;
a semiconductor structure arranged on the conductive substrate, including a first conductive type semiconductor layer, a second conductive type semiconductor layer, and an active layer arranged between the first conductive type semiconductor layer and the second conductive type semiconductor layer, and including a plurality of recesses which pass through the second conductive type semiconductor layer and the active layer, and up to a partial region of the first conductive type semiconductor layer;
a first electrode configured to electrically connect the first conductive type semiconductor layer and the conductive substrate;
a second electrode electrically connected to the second conductive type semiconductor layer; and
an insulating layer arranged in the plurality of recesses, wherein the plurality of recesses include a first recess extending along an outer surface of the semiconductor structure and a plurality of second recesses arranged at an inner side of the first recess,
wherein the first electrode includes a plurality of protruding electrodes extending to the inside of the plurality of second recesses so as to be electrically connected to the first conductive type semiconductor layer,
wherein the active layer includes an inactive area arranged between a side surface of the semiconductor structure and the first recess, and an active area arranged on the inner side of the first recess,
wherein an emission intensity of the inactive area is less than an emission intensity of the active area,
wherein the plurality of second recesses include a plurality of inner recesses in which a number of closest recesses is N and a plurality of outer recesses in which a number of closest recesses is less than N,
wherein the active area includes a second-first region arranged at an outer side based on a closed-loop connecting centers of closest outer recesses among the plurality of outer recesses, and a second-second region arranged at an inner side of the closed-loop, and
wherein a ratio of an emission intensity of the second-second region and an emission intensity of the second-first region is 1:0.5 to 1:0.8.

2. The semiconductor device of claim 1, wherein an electron and a hole are injected into the active area through the first conductive type semiconductor layer and the second conductive type semiconductor layer to generate light with a maximum intensity in an ultraviolet wavelength band.

3. The semiconductor device of claim 2, wherein, in the inactive area, excited electrons due to absorption of light irradiated from the active area or outside emit light through recombination.

4. The semiconductor device of claim 1, wherein an inclination angle of the first recess is the same as an inclination angle of a second recess of the plurality of second recesses.

5. The semiconductor device of claim 4, wherein a height of the first recess and a height of the second recess are the same.

6. The semiconductor device of claim 5, wherein a width of the second recess is larger than a width of the first recess.

7. The semiconductor device of claim 1, wherein a diameter of an outer recess of the plurality of outer recesses is larger than a diameter of an inner recess of the plurality of inner recesses.

8. The semiconductor device of claim 1, wherein a diameter ratio of an inner recess of the plurality of inner recesses and an outer recess of the plurality of outer recesses is 1:1.2 to 1:2.

9. The semiconductor device of claim 1, wherein a shape of an outer recess of the plurality of outer recesses is different from a shape of an inner recess of the plurality of inner recesses.

10. The semiconductor device of claim 9, wherein the plurality of outer recesses have an oval shape.

11. The semiconductor device of claim 1, wherein a ratio of an area of the first recess and an area of a second recess of the plurality of second recesses is 1:6 to 1:10.

12. The semiconductor device of claim 1, wherein the active layer emits an ultraviolet light.

13. The semiconductor device of claim 1, wherein:
a ratio of a maximum area of the semiconductor structure and an area of the first recess is 1:0.01 to 1:0.03; and
the first conductive type semiconductor layer, the second conductive type semiconductor layer, and the active layer include aluminum.

14. A semiconductor device package comprising:
a body; and
a semiconductor device disposed in the body,
wherein the semiconductor device includes: a conductive substrate; a semiconductor structure arranged on the conductive substrate, including a first conductive type semiconductor layer, a second conductive type semiconductor layer, and an active layer arranged between the first conductive type semiconductor layer and the second conductive type semiconductor layer, and including a plurality of recesses which pass through the second conductive type semiconductor layer and the active layer, and up to a partial region of the first conductive type semiconductor layer; a first electrode configured to electrically connect the first conductive type semiconductor layer and the conductive substrate; a second electrode electrically connected to the second conductive type semiconductor layer; and an insulating layer arranged in the plurality of recesses,
wherein the plurality of recesses include a first recess extending along an outer surface of the semiconductor structure and a plurality of second recesses arranged at an inner side of the first recess,
wherein the first electrode includes a plurality of protruding electrodes extending to the inside of the plurality of second recesses so as to be electrically connected to the first conductive type semiconductor layer,
wherein the active layer includes an inactive area arranged between a side surface of the semiconductor structure and the first recess, and an active area arranged on the inner side of the first recess, and
wherein an emission intensity of the inactive area is less than an emission intensity of the active area.

15. The semiconductor device package of claim 14, wherein an electron and a hole are injected into the active area through the first conductive type semiconductor layer and the second conductive type semiconductor layer to generate light with a maximum intensity in an ultraviolet wavelength band.

16. The semiconductor device package of claim 15, wherein, in the inactive area, excited electrons due to absorption of light irradiated from the active area or outside emit light through recombination.

17. The semiconductor device package of claim 14, wherein:
the plurality of second recesses include a plurality of inner recesses in which a number of closest recesses is N and a plurality of outer recesses in which a number of closest recesses is less than N;
the active area includes a second-first region at an outer side based on a closed-loop connecting centers of closest outer recesses among the plurality of outer recesses, and a second-second region arranged at an inner side of the closed-loop; and
a ratio of an emission intensity of the second-second region and an emission intensity of the second-first region is 1:0.5 to 1:0.8.

18. The semiconductor device package of claim 17, wherein a diameter of an outer recess of the plurality of outer recesses is larger than a diameter of an inner recess of the plurality of inner recesses.

* * * * *